(12) United States Patent
Fung et al.

(10) Patent No.: US 6,534,058 B2
(45) Date of Patent: Mar. 18, 2003

(54) ANTI-C5 MONOCLONAL ANTIBODIES

(75) Inventors: Michael S. C. Fung, Houston, TX (US); Bill N. C. Sun, Houston, TX (US); Cecily R. Y. Sun, Houston, TX (US)

(73) Assignee: Tanox, Inc., Houston, TX (US)

( * ) Notice: Subject to any disclaimer, the term of this patent is extended or adjusted under 35 U.S.C. 154(b) by 0 days.

(21) Appl. No.: 09/682,672

(22) Filed: Oct. 4, 2001

(65) Prior Publication Data

US 2002/0041875 A1 Apr. 11, 2002

Related U.S. Application Data

(60) Provisional application No. 60/239,309, filed on Oct. 10, 2000.

(51) Int. Cl.[7] ............... A61K 39/395; C07K 16/36; C12N 5/12
(52) U.S. Cl. ............... 424/158.1; 424/130.1; 424/133.1; 424/141.1; 424/145.1; 424/152.5; 435/326; 435/328; 435/332; 435/346; 435/337; 530/387.1; 530/387.3; 530/388.1; 530/388.2; 530/388.25
(58) Field of Search ............... 424/141.1, 145.1, 424/130.1; 530/387.1, 388.2; 435/452, 326, 332

(56) References Cited

U.S. PATENT DOCUMENTS

| | | | |
|---|---|---|---|
| 5,506,247 A | | 4/1996 | Sindelar et al. |
| 5,679,345 A | | 10/1997 | Sanfilippo et al. |
| 5,851,528 A | | 12/1998 | Ko et al. |
| 5,853,722 A | * | 12/1998 | Rollins et al. |
| 6,196,068 B1 | | 1/2001 | Levin et al. |
| 6,232,293 B1 | | 5/2001 | Anderson et al. |
| 6,319,897 B1 | | 11/2001 | Lambris et al. |
| 6,333,034 B1 | | 12/2001 | Gupta-Bansal et al. |

OTHER PUBLICATIONS

Wang et al., "Complement inhibition with an anti–C5 monoclonal antibody prevents hyperacute rejection in a xenograft heart transplantation model," *Transplantation* 68(11):1643–51 (1999).

Fiane AE, et al., "C1–inhibitor attenuates hyperacute rejection and inhibits complement, leukocyte and platelet activation in an ex vivo pig–to–human perfusion model," *Immunopharmacology* 42(1–3):231–43 (1999).

Linke et al. "Prevention of intial perfusion failure during xenogeneic ex vivo liver perfusion by selectin inhibition," *Transplantation* 66(10):1265–72 (1998).

Jakobs et al., "Prolonged discordant xenograft survival by inhibition of the intrinsic coagulation pathway in complement C6–deficient recipients," *J Heart Lung Transplant* 17(3):306–11 (1998).

Makrides, "Therapeutic inhibition of the complement system," *Pharmacol Rev.* 50(1):59–87 (1998).

Johnson, "Involvement of complement components in renal disease." *Curr Opin Nephrol Hypertens* 6(2):120–7 (1997).

Kroshus et al., "Complement inhibition with an anti–C5 monoclonal antibody prevents acute cardiac tissue injury in an ex vivo model of pig–to–human xenotransplantation," *Transplantation* 60(11):1194–202 (1995).

Davis et al., "Inhibition of neutrophil adhesion and the membrane attack complex of complement synergistically prolongs cardiac xenograft survival," *J Heart Lung Transplant* 14(5):973–80 (1995).

Dalmasso, "The complement system in xenotransplantation," *Immunopharmacology* 24(2):149–60 (1992).

Kuntz Science 257: 1078–1082 (1992).*

* cited by examiner

*Primary Examiner*—Phillip Gambel
(74) *Attorney, Agent, or Firm*—Cheryl A. Liljestrand

(57) ABSTRACT

The invention relates to C5 inhibitors, which inhibit type II endothelial cell activation, wherein the inhibition is manifested by the suppression of E-selectin. These inhibitors are useful in treatment of delayed xenograft rejection or acute vascular rejection. The inhibitors include antibody molecules, as well as homologues, analogues and modified or derived forms thereof, including immunoglobulin fragments like Fab, F(ab')$_2$ and Fv, small molecules, including peptides, oligonucleotides, peptidomimetics and organic compounds. Examples of monoclonal antibodies, which bind to and inhibit C5, were generated and are designated MAb 137-76 and MAb 137-30.

8 Claims, 4 Drawing Sheets

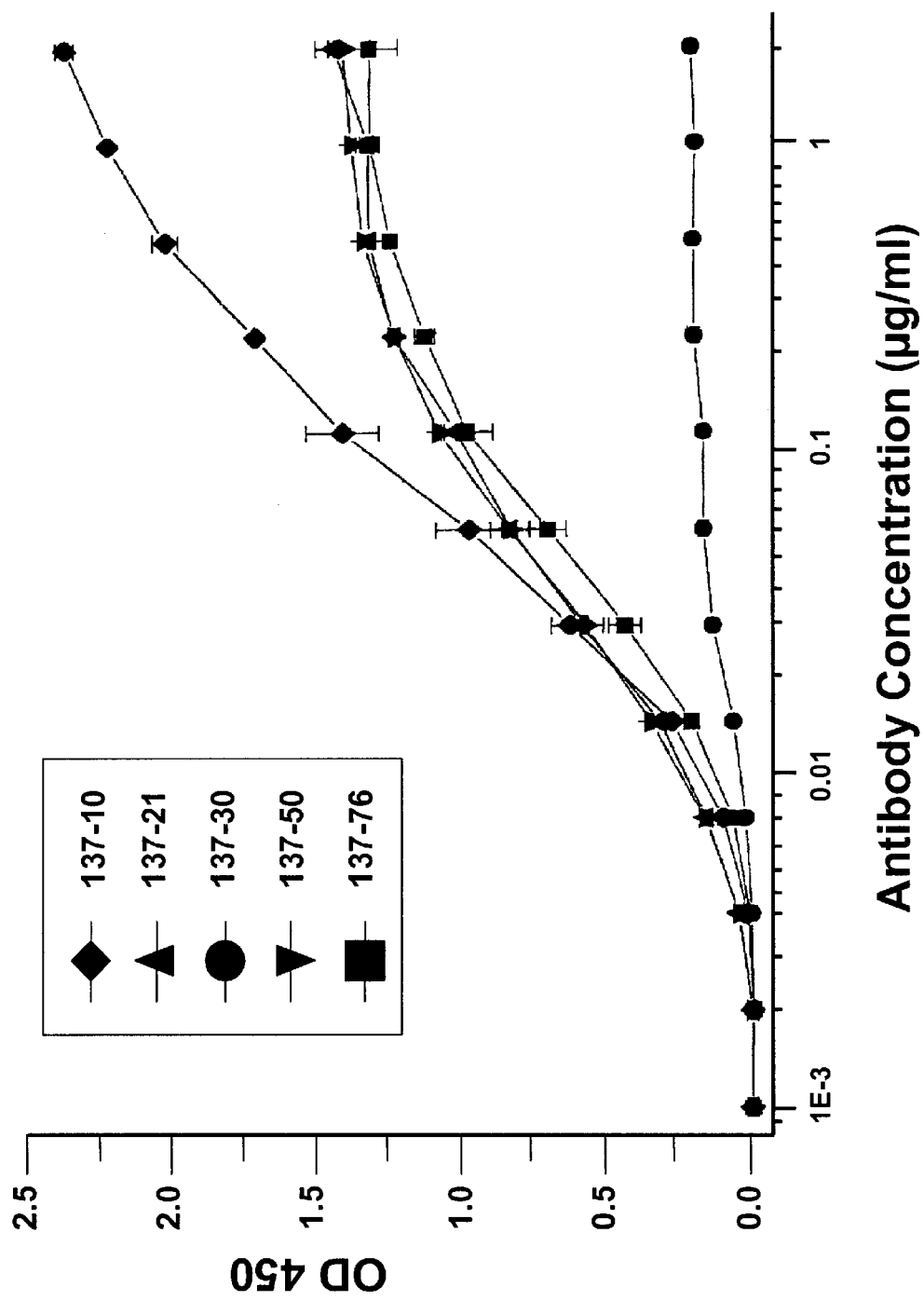
Fig. 1 Reactivity of Anti-C5 MAb with Human C5 in ELISA

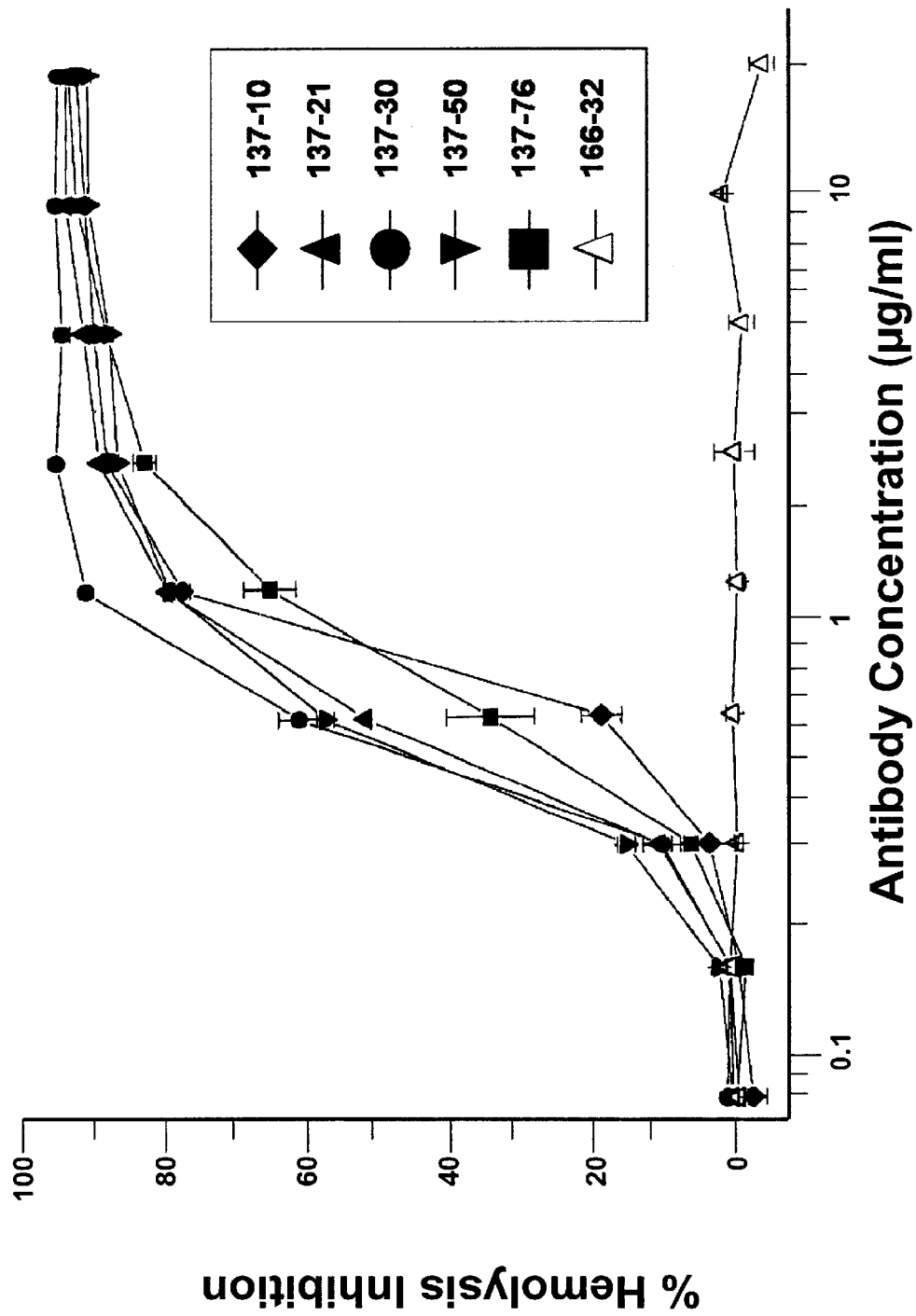
Fig. 2 Inhibition of Classical Pathway Hemolysis by Anti-C5 MAb

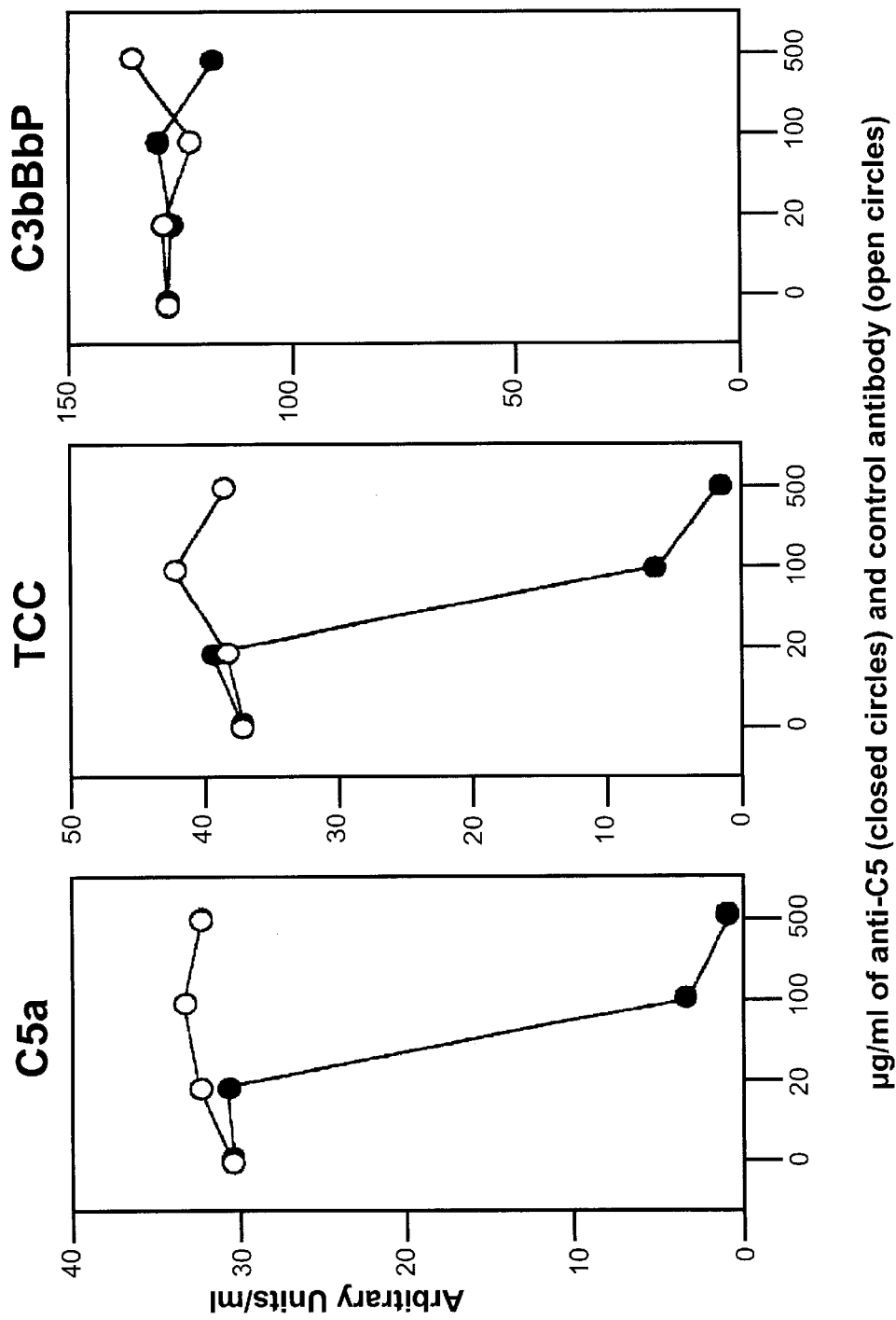
Fig. 3 Anti-C5 MAb 137-76 Inhibits C5a and TCC Production from Human Serum Activated with Zymosan

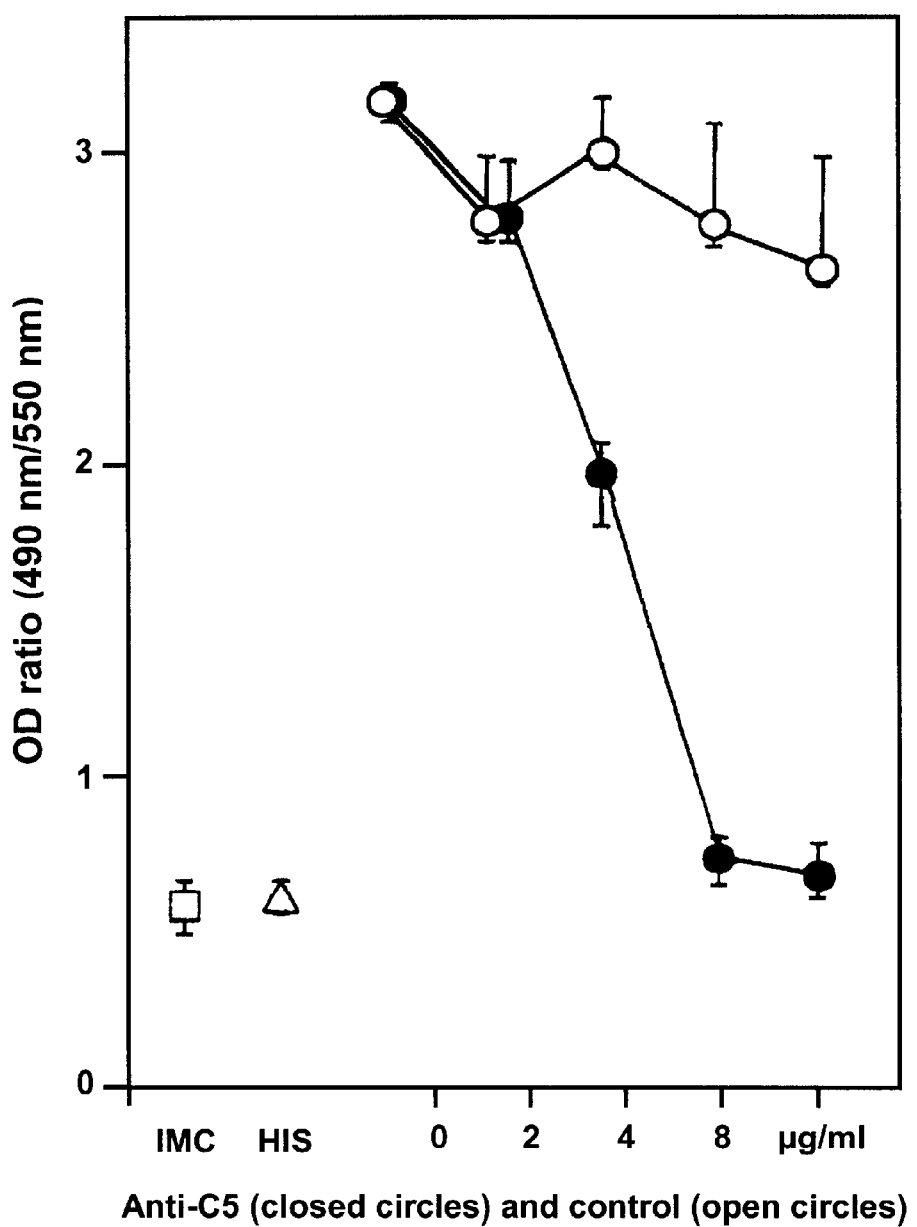
Fig. 4 Anti-C5 MAb 137-76 Inhibits E-selectin Expression on Porcine Aortic Endothelial Cells Exposed to Human Serum

ANTI-C5 MONOCLONAL ANTIBODIES

CROSS REFERENCE TO RELATED APPLICATIONS

This application claims priority to U.S. Provisional Application No. 60/239,309 filed Oct. 10, 2000.

BACKGROUND OF INVENTION

The increased shortage of donor organs has sparked a world-wide interest in xenotransplantation, i.e., the replacement of human organs or tissues with those from a donor of a different species, such as pigs. Recent progress offers cause for optimism, but there are obstacles that must be overcome.

Xenotransplants have been classified into two groups, concordant and disconcordant, based on the phylogenetic distance between species. Animals that are evolutionarily close and do not have natural antibodies specific for each other are termed concordant. Animals that are phylogenetically distant and reject organs in a hyperacute manner are termed discordant. There are many gradations in between and exceptions to the rule.

Non-human primates would be the logical source of organs for humans, in that they are most closely related. However, due to considerations of size of the organ, lack of availability, and the likelihood of transmission of infectious diseases, most researchers have determined that primates are not a preferred source of organs. Instead, the swine is the likely choice for a source of organs, because of its ready availability, similarity in organ size, its breeding characteristics, and the similarity of its organ systems to humans. However, the swine is a discordant species to humans.

Xenografts are subject to all four rejection mechanisms: (1) hyperacute rejection mediated by preformed antibodies, (2) early or accelerated rejection mediated by induced antibodies, (3) delayed xenograft rejection or acute vascular rejection (DXR/AVR) mediated by T-cells, and (4) chronic rejection mediated by B-cell and T-cell mechanisms. Induction of all four mechanisms can be attributed to a greater number of foreign antigens present than in an allograft tissue (one from the same species, i.e., human). Further, human inhibitory receptors often do not interact with the other species' class I MHC molecules, thus allowing the activation of various rejection mechanisms that proceed uninhibited. Transplantation of porcine pancreatic islets and of a pig liver into human patients has been reported, (Makowka, et al., 1993; Satake, et al., 1993; Tibell, et al., 1993), but the outcomes were not positive. Improved inhibition of transplant rejection with drug therapy may lead to better outcomes.

Hyperacute rejection of xenografts is initiated by the binding of xenoreactive antibodies to donor endothelial cells followed by the activation of complement, predominaritly via the classical pathway. Pigs, for example, express an endothelial carbohydrate determinant, gal α (1,3) gal, that is not expressed in humans, and is considered a new blood group antigen to the human immune system. Complement activation induces type I activation of the endothelial cells, a process which is rapid and independent of protein synthesis. It is characterized by reversible cell retraction, translocation of P-selectin to the apical surface, and the elaboration of a variety of vasoactive substances. Furthermore, heparin sulphate proteoglycans are released from the endothelial cell surface leaving the cell susceptible to procoagulant and complement-mediated injury. Critical functions of endothelial cells are lost, and the end-result is interstitial hemorrhage, diffuse thrombosis, and irreversible organ damage occurring from within minutes to several hours following transplant. These are the characteristic features of HAR. HAR can be prevented by reducing either complement activity or the level of naturally occurring anti-xenograft antibodies.

Even if one reduces or eliminates HAR, the xenograft will be rejected after a few days by the process designated delayed xenograft rejection or acute vascular rejection (DXR/AVR). DXR/AVR is characterized by type II endothelial cell activation, which is protein synthesis dependent. Although DXR/AVR is thought to be largely complement independent, some studies indicate that complement may still be involved in DXR/AVR. Inhibition of complement by soluble complement receptor type I (sCR1) combined with immunosuppression delayed the occurrence of DXR/AVR of porcine hearts transplanted into cynomolgus monkeys (Davis, EA et al., *Transplantation* 62:1018–23 (1996)). Transplantation of pig kidneys expressing human decay accelerating factor to cynomolgus monkeys also had some protective effect against DXR/AVR (Zaidi A et al. *Transplantation* 65:1584–90 (1998); Loss M et al., *Xenotransplantation* 7: 186–9(2000)). Addition of anti-endothelial cell antibodies and complement in sublytic doses induced expression of tissue factor (Saadi S et al., *J. Exp. Med.* 182:1807–14 (1995)). Porcine endothelial cells exposed to human serum expressed plasminogen activator inhibitor (Kalady M F et al., *Mol. Med.* 4:629–37 (1998)) and increased the expression of various chemokine genes (Selvan RS et al., *J. Immunol.* 161:4388–95 (1998)). The increased expression of various chemokine genes was found to be complement dependent. Nevertheless, an anti-C5 monoclonal antibody was shown to be effective in preventing HAR, but not DXR/AVR (Wang, H. et al., *Transplantation* 68:1643–51 (1999)).

E-selectin (also known as ELAM-1, CD62, and CD62E) is a cytokine inducible cell surface glycoprotein cell adhesion molecule that is found exclusively on endothelial cells. E-selectin mediates the adhesion of various leukocytes, including neutrophils, monocytes, eosinophils, natural killer (NK) cells, and a subset of T cells, to activated endothelium (Bevilacqua, et al., *Science* 243: 1160 (1989); Shimuzu, et al., *Nature* 349:799 (1991); Graber, et al., *J. Immunol.* 145: 819 (1990); Carlos, et al., *Blood* 77: 2266 (1991); Hakkert, et al., *Blood* 78:2721 (1991); and Picker, et al., *Nature* 349:796 (1991)). The expression of E-selectin is induced on human endothelium in response to the cytokines IL-1 and TNF, as well as bacterial lipopolysaccharide (LPS), through transcriptional upregulation (Montgomery, et al., *Proc Natl Acad Sci* 88:6523 (1991)).

The human leukocyte receptor for human E-selectin has been identified (Berg, et al., *J. Biol. Chem.* 23: 14869 (1991) and Tyrrell, et al., *Proc Natl Acad Sci* 88:10372 (1991)). Structurally, E-selectin belongs to a family of adhesion molecules termed "selecting" that also includes P-selectin and L-selectin (see reviews in Lasky, *Science* 258:964 (1992) and Bevilacqua and Nelson, *J. Clin. Invest.* 91:379 (1993)). These molecules are characterized by common structural features such as an amino-terminal lectin-like domain, an epidermal growth factor (EGF) domain, and a discrete number of complement repeat modules (approximately 60 amino acids each) similar to those found in certain complement binding proteins.

Clinically, increased E-selectin expression on endothelium is associated with a variety of acute and chronic leukocyte-mediated inflammatory reactions including allograft rejection (Allen, et al., *Circulation* 88: 243 (1993);

Brockmeyer, et al., *Transplantation* 55:610 (1993); Ferran, et al *Transplantation* 55:605 (1993); and Taylor, et al., *Transplantation* 54: 451 (1992)). Studies in which the expression of human E-selectin in cardiac and renal allografts undergoing acute cellular rejection was investigated have demonstrated that E-selectin expression is selectively upregulated in vascular endothelium of renal and cardiac tissue during acute rejection. Id. Additionally, increased E-selectin expression correlates with the early course of cellular rejection and corresponds to the migration of inflammatory cells into the graft tissue. Id. Taken together, these studies provide evidence that cytokine-induced expression of E-selectin by donor organ endothelium contributes to the binding and subsequent transmigration of inflammatory cells into the graft tissue and thereby plays an important role in acute cellular allograft rejection.

Blocking the upregulation of E-selectin, which is a major hallmark for type II endothelial cell activation characteristic of DXR/AVR, would be a potential strategy to treat and prevent DXR/AVR.

SUMMARY OF INVENTION

The invention includes C5 inhibitors that bind to C5 and inhibit type II endothelial cell activation, as well as suppressing the upregulation of E-selectin on endothelial cells. These C5 inhibitors are useful for the treatment and prevention of xenograft rejection, and in particular DXR/AVR. The C5 inhibitors may also inhibit the formation of C5a, inhibit the formation of Terminal Complement Complex ("TCC") and/or block complement mediated cell lysis. The inhibitors include monoclonal antibodies ("MAb") as well as homologues, analogues and modified or derived forms thereof, including immunoglobulin fragments like Fab, $F(ab')_2$, Fv and single chain antibodies. Small molecules including peptides, oligonucleotides, peptidomimetics, and organic compounds with the same functional activity are also included.

One example of a MAb which bound to C5 was shown, in an in vitro model, to be useful in treatment of xenograft rejection and DXR/AVR, was generated as described below and designated 137-76. Other examples include the Anti-C5 MAbs 137-10, 137-21, 137-30, and 137-50. The invention also includes monoclonal antibodies that bind to the same epitope as either MAb 137-76 or MAb 137-30.

The treatment of delayed xenograft rejection or acute vascular rejection involves the administration of a C5 inhibitor of the invention that inhibits type II endothelial cell activation and which can be manifested by the suppression of E-selectin expression.

BRIEF DESCRIPTION OF DRAWINGS

FIG. 1 shows the binding of the anti-C5 antibodies to human C5 in ELISA as a function of antibody concentration (See Example 1). MAb 137-76 exhibited strong binding with human C5.

FIG. 2 shows the inhibition of classical pathway hemolysis by anti-C5 antibodies (See Example 2). Anti-C5 MAbs 137-10, 137-21, 137-30, 137-50, and 137-76 strongly inhibit classical pathway hemolysis. MAb 166-32 binds to Factor D, which is involved in the alternative complement pathway and is acting as a control here, and therefore, does not show inhibition of classical pathway hemolysis.

FIG. 3 shows the inhibition of C5 activation by the anti-C5 MAb 137-76 in human serum (10%) activated with zymosan (See Example 3). The Y-axis represents values given in arbitrary units (AU) using a standard of 100% zymosan-activated serum defined to contain 1000 AU/ml. X-axis represent the concentration of the test and negative control antibodies. MAb 137-76 inhibits the formation of C5a and TCC (markers for C5 activation), but not C3bBbP (an alternative pathway marker), whereas MAb G3-519, an HIV-1 protein with no involvement in complement activation, does not inhibit the formation of C5a, TCC, or C3bBbP.

FIG. 4 shows the inhibition of E-selectin expression in porcine aortic endothelial cells. Isolated porcine aortic endothelial cells were treated with human serum (25%) (See Example 4). The anti-C5 Mab 137-76, represented by closed circles, completely inhibits upregulation of E-selectin in a dose-dependent manner. The irrelevant isotype-matched control MAb G3-519, represented by open circles, does not inhibit the expression of E-selectin. Open triangles represent E-selectin expression on cells incubated with heat-inactivated serum (HIS). Open squares represent E-selectin expression on cells incubated in the absence of human serum (IMC). Y-axis represents the expression level of E-selectin in OD ratios normalized for the amount of endothelial cells in each well.

DETAILED DESCRIPTION

Biological Deposit Data

[ID: b3]
Oct. 11, 2000
30 Years
American Type Culture Collection
10801 University Blvd.
Manassas
Va.
20110-2209
United States
703-365-2700 703-365-2745 PTA-2581 Hybridoma producing monoclonal antibody designated 137-76.

[ID: b5]
Oct. 11, 2000
30 Years
American Type Culture Collection
10801 University Blvd.
Manassas
Va.
20110-2209
United States
703-365-2700 703-365-2745 PTA-2582 Hybridoma producing the monoclonal antibody designated 137-30.

The complement system plays a central role in the clearance of immune complexes and in immune responses. Excessive activation of the complement system by a xenograft can lead to harmful, and even potentially life-threatening, consequences due to severe inflammation and resulting tissue destruction.

Activation of the complement pathway generates biologically active fragments of complement proteins, e.g. C3a, C4a and C5a anaphylatoxins and C5b-9 membrane attack complexes (MAC), which mediate inflammatory responses through involvement of leukocyte chemotaxis, activation of macrophages, neutrophils, platelets, mast cells and endothelial cells, vascular permeability, cytolysis, and tissue injury. Complement C5a is one of the most potent proinflammatory mediators of the complement system. C5a is the activated form of C5.

The invention includes MAbs that bind to and inhibit the activation C5. In addition to monoclonal antibodies, the invention includes homologues, analogues and modified or derived forms thereof, including immunoglobulin fragments like Fab, F(ab')$_2$, Fv and single chain antibodies. Also included are molecules including peptides, oligonucleotides, peptidomimetics and organic compounds.

The term analogue is commonly used to refer to Fab, ScFv, or other fragments with the same binding regions, therefore the same functionality to a defined antigen, as the antibody for which it is an analog. The antigen in this case is C5. The term homologue is commonly used to refer to entities with similar amino acid sequences or structures, e.g. different isotypes of immunoglobulins IgA, IgG, IgE, etc.

Monoclonal Antibodies

Monoclonal antibodies may be made using the hybridoma method first described by Kohler et al., *Nature*, 256:495 (1975), or by other well-known, subsequently-developed methods.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, Calif. USA, and SP2/0 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al., Monoclonal Antibody Production Techniques and Applications, pp. 51–63 (Marcel Dekker, Inc., New York, 1987)). The mouse myeloma cell line NSO may also be used (European Collection of Cell Cultures, Salisbury, Wiltshire UK).

The culture medium in which hybridoma cells are grown is assayed for production of monoclonal antibodies directed against the antigen. The binding specificity of monoclonal antibodies produced by hybridoma cells may be determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (Innis M. et al. In PCR Protocols. A Guide to Methods and Applications, Academic, San Diego, Calif. (1990), Sanger, F. S, et al. *Proc. Nat. Acad. Sci.* 74:5463–5467 (1977)). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

Antibodies or antibody fragments can be isolated from antibody phage libraries generated using the techniques described in McCafferty, et al., *Nature* 348:552–554 (1990). Clackson, et al., *Nature* 352:624–628 (1991) and Marks, et al., *J. Mol. Biol.* 222:581–597 (1991) describe the isolation of murine and human antibodies, respectively, using phage libraries. Subsequent publications describe the production of high affinity (nM range) human antibodies by chain shuffling (Marks, et al., *Bio/Technology* 10:779–783 (1992)), as well as combinatorial infection and in vivo recombination as a strategy for constructing very large phage libraries (Waterhouse, et al., *Nuc. Acids. Res.* 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Nat. Acad. Sci. USA* 81: 6851 (1984)).

Another alternative is to use electrical fusion rather than chemical fusion to form hybridomas. This technique is well established. Instead of fusion, one can also transform a B-cell to make it immortal using, for example, an Epstein Barr Virus, or a transforming gene. (See, e.g., "Continuously Proliferating Human Cell Lines Synthesizing Antibody of Predetermined Specificity," Zurawaki, V. R. et al, in Monoclonal Antibodies, ed. by Kennett R. H. et al, Plenum Press, N.Y. 1980, pp 19–33.) Anti-C5 MAbs can be raised by immunizing rodents (e.g. mice, rats, hamsters and guinea pigs) with either native C5 purified from human plasma or serum, recombinant C5 or its fragments expressed by either eukaryotic or prokaryotic systems. Other animals can be used for immunization, e.g. non-human primates, transgenic mice expressing human immunoglobulins and severe combined immunodeficient (SCID) mice transplanted with human B lymphocytes. Hybridomas can be generated by conventional procedures by fusing B lymphocytes from the immunized animals with myeloma cells (e.g. Sp2/0 and NSO), as described earlier (Köhler G et al., *Nature* 256:

495–7 (1975)). In addition, anti-C5 antibodies can be generated by screening of recombinant single-chain Fv or Fab libraries from human B lymphocytes in phage-display systems. The specificity of the MAbs to human C5 can be tested by enzyme linked immunosorbent assay (ELISA), as shown in FIG. 1, Western immunoblotting, or other immunochemical techniques. The inhibitory activity of the antibodies on complement activation can be assessed by hemolytic assays, using sensitized chicken or sheep RBCs for the classical complement pathway. The hybridomas in the positive wells are cloned by limiting dilution. The antibodies are purified for characterization for specificity to human C5 by the assays described above.

Humanized and Human Antibodies

A humanized antibody is designed to have greater homology to a human immunoglobulin than animal-derived monoclonal antibodies. Non-human amino acid residues from an "import" (animal) variable domain are transfected into a human "backbone". Humanization can be essentially performed following the method of Winter and co-workers (Jones et al., Nature 321:522–525 (1986); Riechmann et al ., Nature 332:323–327 (1988); Verhoeyen, et al., Science, 239:1534–1536 (1988)), by substituting rodent complementarity determining regions ("CDRs") or CDR sequences for the corresponding sequences of a human antibody. Accordingly, in such "humanized" antibodies, the CDR portions of the human variable domain have been substituted by the corresponding sequence from a non-human species. Thus, humanized antibodies are typically human antibodies in which some CDR residues and possibly some framework residues are substituted by residues from analogous sites in rodent antibodies.

The choice of human variable domains, both light and heavy, to be used in making the humanized antibodies is important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that humanized antibodies retain high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of certain residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is maximized, although it is the the CDR residues that directly and most substantially influence antigen binding.

One can also produce transgenic animals (e.g., mice) that are capable, upon immunization, of producing a full repertoire of human antibodies in the absence of endogenous immunoglobulin production. Such transgenic mice are available from Abgenix, Inc., Fremont, Calif., and Medarex, Inc., Annandale, N.J. It has been described that the homozygous deletion of the antibody heavy-chain joining region (IH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA 90:2551 (1993); Jakobovits et al., Nature 362:255–258 (1993); Bruggermann et al., Year in Immunol. 7:33 (1993); and Duchosal et al. Nature 355:258 (1992). Human antibodies can also be derived from phage-display libraries (Hoogenboom et al ., J. Mol. Biol. 227: 381 (1991); Marks et al., J. Mol. Biol. 222:581–597 (1991); Vaughan, et al., Nature Biotech 14:309 (1996)).

Chimeric antibodies are produced by recombinant processes well known in the art, and have an animal variable region and a human constant region. Humanized antibodies have a greater degree of human peptide sequences than do chimeric antibodies.

One can also create single peptide chain binding molecules in which the heavy and light chain Fv regions are connected. Single chain antibodies ("scFv") and the method of their construction are described in U.S. Pat. No. 4,946,778. Alternatively, Fab can be constructed and expressed by similar means (Evans M J et al. Rapid expression of an anti-human C5 chimeric Fab utilizing a vector that replicates in COS and 293 cells. J. Immunol. Meth. 184: 123–38 (1995)). All of the wholly and partially human antibodies are less immunogenic than wholly murine MAbs, and the fragments and single chain antibodies are also less immunogenic.

DeImmunised™ Antibodies

DeImmunised™ antibodies are antibodies in which the potential T cell epitopes have been eliminated, as described in International Patent Application PCT/GB98/01473. Therefore, immunogenicity in humans is expected to be eliminated or substantially reduced when they are applied in vivo. Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546, which are all hereby incorporated by reference in their entireties. Preferred polymers are polyoxyethylated polyols and polyethylene glycol (PEG). PEG is soluble in water at room temperature and has a preferred average molecular weight between 1000 and 40,000, more preferably between 2000 and 20,000, most preferably between 3,000 and 12,000.

If used in treating xenograft rejection, in particular DXR/AVR in humans, the anti-C5 antibodies would preferably be used as chimeric, Deimmunised, humanized or human antibodies. Such antibodies can reduce immunogenicity and thus avoid human anti-mouse antibody (HAMA) response. It is preferable that the antibody be IgG4, IgG2, or other genetically mutated IgG or IgM which does not augment antibody-dependent cellular cytotoxicity (Canfield S M et al., *J. Exp. Med.* 173: 1483–91 (1991)) and complement mediated cytolysis (Xu Y et al., *J. Biol. Chem.* 269: 3468–74 (1994); Pulito V L et al., *J. Immunol.* 156: 2840–2850 (1996)).

Based on the molecular structures of the variable regions of the anti-C5 antibodies, one could use molecular modeling and rational molecular design to generate and screen small molecules which mimic the molecular structures of the binding region of the antibodies and inhibit the activities of C5. These small molecules can be peptides, peptidomimetics, oligonucleotides, or organic compounds. The mimicking molecules can be used as inhibitors of complement activation in inflammatory indications and autoimmune diseases. Alternatively, one could use large-scale screening procedures commonly used in the field to isolate suitable small molecules form libraries of combinatorial compounds.

Making Other C5 Inhibitors of the Invention

In another aspect of this invention, libraries containing mimetics of the present invention are disclosed. Once assembled, the libraries of the present invention may be screened to identify individual members having bioactivity. Such screening of the libraries for bioactive members may involve, for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with C5 are referred to herein as "bioactive library members" or "bioactive mimetics". For example, a bioactive mimetic may be a library member which is capable of binding and inhibiting C5 or which is capable of antagonizing a functional response associated with C5. In other words, the screening of the libraries of the present invention determines which library members are capable of interacting with C5. Furthermore, when interaction does occur, the bioactive mimetic (or mimetics) may then be identified from the library members. The identification of a single (or limited number) of bioactive mimetic(s) from the library yields mimetics which are themselves biologically active, and thus useful as diagnostic, prophylactic or therapeutic agents, and may further be used to significantly advance identification of lead compounds in these fields.

Synthesis of the peptide mimetics of the library of the present invention may be accomplished using known peptide synthesis techniques. The mimetics may be synthesized on a solid support (such as polystyrene utilizing 4 as a linker) by known techniques (see, e.g., John M. Stewart and Janis D. Young, Solid Phase Peptide Synthesis, 1984, Pierce Chemical Comp., Rockford, Ill.; Atherton, E., Shepard, R. C. Solid Phase Peptide Synthesis: A Practical Approach; IRL: Oxford, 1989) or on a silyl-linked resin by alcohol attachment (see Randolph et al., J Am. Chem. Soc. 117:5712–14, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained reverse-turn is added to the sequence. Traditional combinatorial chemistry (see, e.g., The Combinatorial Index Bunin, Academic Press, New York, 1998; Gallop et al., J Med. Chem. 37:1233–1251, 1994) and parallel synthesis techniques permit a vast number of compounds to be rapidly prepared by the sequential combination of reagents to a basic molecular scaffold. For example, the above disclosed synthesis may be carried out using the directed sorting technique of Nicolaou and coworkers. (Nicolaou et al., Angew. Chem. Int'l. Ed. 34:2289–2291, 1995). Presently, equipment for this technique is commercially available from IRORI (La Jolla, Calif.). Alternatively, the above disclosed synthesis may be carried out by parallel synthesis using a 48- or 98-well plate format wherein each well contains a fritted outlet for draining solvents and reagents (A Practical Guide to Combinatorial Chemistry Czarnik and DeWitt, Eds., American Chemical Society, Washington, D.C., 1997). Robbins (Sunnyvale, Calif.), Charybdis (Carlsbad, Calif.) and Bohdan (Chicago, Ill.) presently offer suitable equipment for this technique.

Methods for screening the libraries for bioactivity and isolating bioactive library members are disclosed. The libraries of the present invention may be screened for bioactivity by a variety of techniques and methods. Generally, the screening assay may be performed by (1) contacting a library with C5, or a fragment thereof, and allowing binding to occur between the mimetics of the library and the target, and (2) detecting the binding event by an appropriate assay, such as by the colorimetric assay disclosed by Lam et al. (Nature 354:82–84, 1991) or Griminski et al. (Biotechnology 12:1008–1011, 1994). The library members may be in solution and the target immobilized on a solid phase. Alternatively, the library may be immobilized on a solid phase and may be probed by contacting it with the target in solution.

An automated system for generating and screening a compound library is described in U.S. Pat. Nos. 5,901,069 and 5,463,564. More focused approaches involve a competitive screen against the MAb 137-76, or making a three-dimensional model of the binding site, and then making a family of molecules which fit the model. These are then screened for those with optimal binding characteristics. In addition, other molecules may be identified by competition assay, or a functional screen for inhibitors with the same properties as MAb137-76.

Application of Anti-C5 Molecules

The anti-C5 binding molecules, antibodies, and fragments of this invention, can be administered to patients in an appropriate pharmaceutical formulation by a variety of routes, including, but not limited, intravenous infusion, intravenous bolus injection, and intraperitoneal, intradermal, intramuscular, subcutaneous, intranasal, intratracheal, intraspinal, intracranial, and oral routes. Such administration enables them to bind to endogenous C5 and thus inhibit C5 activation.

The estimated preferred dosage of such antibodies and molecules is between 10 and 500 µg/ml of serum. The actual dosage can be determined in clinical trials following the conventional methodology for determining optimal dosages, i.e., administering various dosages and determining which is most effective.

The anti-C5 molecules can function to inhibit in vivo complement activation and inflammatory manifestations that accompany it, such as recruitment and activation of macrophages, neutrophils, platelets, mast cells and endothelial cells, edema, and tissue damage. These inhibitors can be used for prevention of xenograft rejection, including the DXR/AVR response to xenografts.

The anti-C5 molecules can also be used diagnostically to ascertain the presence of, or to measure, C5 in a tissue specimen or a body fluid sample, such as serum, plasma, urine or spinal fluid. In this application, common assay formats can be used, such as immunohistochemistry or ELISA, respectively. Such diagnostic tests could be useful in determining whether certain individuals are either deficient in or overproduce C5.

Animal Models of the Therapeutic Efficacy of C5 Inhibitors

The therapeutic activity of C5 inhibitors for treatment and prevention of DXR/AVR in xenotransplantation can be tested in established animal models (Davis EA et al., Transplantation 62: 1018–23 (1996); Wang H et al., Transplantation 68: 1644–51 (1999); Loss M et al., Xenotransplantation 7: 186–96 (2000)).

EXAMPLE 1

Generation of Anti-C5 MAbs

Male A/J mice (Harlan, Houston, Tex.), 8–12 weeks old, were injected subcutaneously with 20 µg of C5 in complete Freund's adjuvant (Difco Laboratories, Detroit, Mich.) in 200 µl of phosphate-buffered saline (PBS) pH7.4. C5 purified from human plasma was purchased from Advanced Research Technologies, Inc. (San Diego, Calif.). At two-week intervals, the mice were twice injected subcutaneously with 20 µg of C5 in incomplete Freund's adjuvant on two occasions: Then, two weeks later and three days prior to sacrifice, the mice were again injected intraperitoneally with 20 µg of the same antigen in PBS. For each fusion, single cell suspensions were prepared from the spleen of an immunized mouse and used for fusion with Sp2/0 myeloma cells. $5 \times 10^8$ of the Sp2/0 and $5 \times 10^8$ spleen cells were fused in a medium containing 50% polyethylene glycol (M.W. 1450) (Kodak, Rochester, N.Y.) and 5% dimethylsulfoxide (Sigma Chemical Co., St. Louis, Mo.). The cells were then adjusted to a concentration of $1.5 \times 10^5$ spleen cells per 200 µl of the suspension in Iscove medium (Gibco, Grand Island, N.Y.), supplemented with 10% fetal bovine serum, 100 units/ml of penicillin, 100 µg/ml of streptomycin, 0.1 mM hypoxanthine, 0.4 µM aminopterin, and 16 µM thymidine. Two hundred microliters of the cell suspension were added to each well of about fifty 96-well microculture plates. After about ten days culture supernatants were withdrawn for screening for reactivity with purified C5 in ELISA.

Wells of Immulon 2 (Dynatech Laboratories, Chantilly, Va.) microtest plates were coated by adding 50 µl of purified human C5 at 0.1 µg/ml overnight at room temperature. After the coating solution was removed by flicking of the plate, 200 µl of BLOTTO (non-fat dry milk) in phosphate-buffered saline (PBS) was added to each well for one hour to block the non-specific sites. An hour later, the wells were then washed with a buffer PBST (PBS containing 0.05% Tween 20). Fifty microliters of culture supernatants from each fusion well were collected, mixed with 50 µl of BLOTTO and then added to the individual wells of the microtest plates. After one hour of incubation, the wells were washed with PBST. The bound murine antibodies were then detected by reaction with horseradish peroxidase (HRP) conjugated goat anti-mouse IgG (Fc specific) (Jackson ImmunoResearch Laboratories, West Grove, Pa.) and diluted at 1:2,000 in BLOTTO. Peroxidase substrate solution containing 0.1% 3,3,5,5-tetramethyl benzidine (Sigma) and 0.0003% hydrogen peroxide (Sigma) was added to the wells for color development for 30 minutes. The reaction was terminated by addition of 50 µl of 2M $H_2SO_4$ per well. The OD at 450 nm of the reaction mixture was read with a BioTek ELISA Reader (BioTek Instruments, Winooski, VT.).

The culture supernatants from the positive wells were then tested for inhibition of classical pathway hemolysis of sensitized chicken RBCs by pre-titered human serum (2%) by the method described below. The cells in those positive wells were cloned by limiting dilution. The MAbs were tested again for reactivity with C5 in the ELISA. The selected hybridomas were grown in spinner flasks and the spent culture supernatant collected for antibody purification by protein A affinity chromatography. Five MAbs were tested to be reactive with human C5 in ELISA. These MAbs are designated 137-10, 137-21, 137-30, 137-50, 137-76 (FIG. 1). Among them, MAb 137-76 is most reactive with solid-phase human C5, whereas 137-30 is least reactive with solid-phase human C5. These anti-C5 MAb were tested to be not reactive with human C5a in ELISA. MAb 137-76 does not compete with the binding of MAb 137-30 to human C5 in ELISA, indicating that these two antibodies bind to distinct epitopes on human C5.

EXAMPLE 2

Inhibition of Complement-activated Hemolysis by Anti-C5 MAbs

The anti-C5 MAbs were tested for inhibition of the classical complement in hemolytic assays. In the assays, chicken red blood cells (RBCs) ($5 \times 10^7$ cells/ml) in gelatin/veronal-buffered saline (GVB$^{++}$) containing 0.5 mM MgCl$^2$ and 0.15 mM CaCl$_2$ were sensitized with purified rabbit anti-chicken RBC immunoglobulins at 8 µg/ml (Inter-Cell Technologies, Hopewell, N.J.) for 15 minutes at 4° C. The cells were then washed with GVB$^{++}$. The washed cells were resuspended in the same buffer at $1.7 \times 10^8$ cells/ml. In each well of a round-bottom 96-well microtest plate, 50 µl of normal human serum (2%) was mixed with 50 µl of GVB$^{++}$ or serially diluted test MAb, then 30 µl of the washed sensitized chicken RBC suspension were added to the wells containing the mixtures. Fifty microliters of normal human serum (2%) was mixed with 80 µl of GVB$^{++}$ to give the serum color background. The final mixture was incubated at 37° C. for 30 minutes. The plate was then shaken on a micro-test plate shaker for 15 seconds. The plate was then centrifuged at 300×g for 3 minutes. Supernatants (80 µl) were collected and transferred to wells on a flat-bottom 96-well microtest plates for measurement of OD at 405 nm. The percent inhibition of hemolysis is defined as 100× [($OD_{without\ MAb} OD_{serum\ color\ background}$)($OD_{with\ MAb\ serum\ color\ background}$)]/$OD_{without\ MAb} OD_{serum\ color\ background}$.

FIG. 2 shows the data that the anti-C5 MAbs 137-10, 137-21, 137-30, 137-50, 137-76 strongly inhibit the classical pathway hemolysis. The anti-factor D MAb 166-32 which is specific for inhibition of the alternative complement pathway, does not inhibit the hemolysis of the classical pathway, as expected.

EXAMPLE 3

Inhibition of C5 Activation by Anti-C5 MAbs in Human Serum Activated With Zymosan To study the effects of anti-C5 MAb 137-76 on C5 activation, we measured the inhibition of the formation of C5a and TCC (terminal C5b-9 complement complex) in human serum activated with zymosan (yeast particle) via the alternative complement pathway. Different concentrations of anti-C5 MAb 137-76 were added to human serum (10%) activated with zymosan (1 mg/ml). An isotype-matched control MAb G3-519 was used as negative control. MAb G3-519 is specific to HIV-1 external envelope glycoprotein gp 120 and has no effects on complement activity. The activation products C5a, TCC, and C3bBbP were measured by quantitative ELISAs. C5a and TCC are the specific markers for the activation of C5, whereas C3bBbP, the alternative C3/C5 convertase, for the activation of the alternative complement pathway. The ELISAs for C5a and TCC determination have been described in detail previously (Bergh K et al., *J. Immunol. Meth.* 152: 79–97 (1992); Mollnes TE et al., Scand. *J. Immunol.* 22: 197–202 (1985)) .The ELISA for the alternative convertase C3bBbP was performed as follows: Capture Mab immobilized on 96-well microtest plastic plates was mouse monoclonal anti-human properdin antibody (clone #2) diluted 1:1000 (Quidel, San Diego, Calif.). Test samples were diluted 1:25. Detection was made by using polyclonal rabbit anti-human C3c diluted 1:1000 (Behringwerke A/G, Marburg, Germany), and then horseradish peroxidase-conjugated anti-rabbit lg diluted 1:1000 (Amersham International, Little Chalfont, United Kingdom).

The results show that MAb 137-76 completely inhibits C5 activation, as evidenced by the inhibition of the production of C5 activation products, C5a and TCC (FIG. 3). On the contrary, the antibody has no effect on the formation of the alternative C3/C5 convertase C3bBbP, which is upstream of the C5 step in the complement cascade.

EXAMPLE 4

Inhibition of Human Serum-induced Upregulation of E-selectin on Porcine Aortic Endothelial Cells Type II endothelial cell activation is a hallmark of DXR/AVR. Upregulation of E-selectin on endothelial cells is one of the characteristics of type II endothelial cell activation. We examined the effects of anti-C5 MAb 137-76 on human serum-induced upregulation of E-selectin on isolated porcine aortic endothelial cells (PAEC).

a. Preparation of PAEC Culture

Porcine aortae were obtained from a local slaughterhouse (Fellesslakteriet, Ø kern, Oslo, Norway). The vessel was cut distal to the aortic arch with a sterile surgical scissors and immediately placed into a sterile beaker containing endothelial cell buffer, 2.5 µg/ml amphotericin β and 50 µg/ml gentamycin. The aortae were transported to the laboratory within 30 minutes, and transferred to a second beaker containing fresh endothelial cell buffer with antibiotics at 4° C. The intercostal vessels were clamped with LigaClip (Johnson & Johnson Company, Ethicon, Cincinnati, Ohio) before PAEC were isolated by collagenase treatment (0.1% collagenase A (Boehringer Mannheim, Mannheim, Germany), at 37° C., for 4–8 minutes). Isolated PAEC were suspended in the medium Endothelial-SFM (Life Technologies, Paisley, Scotland), containing 5% fetal calf serum and antibiotics, and plated in gelatin-coated (1%) culture flasks (25 cm$^2$). The content of serum and amphotericin β was reduced to 1% and 0.5 µg/ml after one and seven days in culture, respectively. Subconfluent primary cultures were trypsinized and cultured to confluence in the first passage before being frozen for storage in aliquots.

b. In Vitro Porcine-to-Human Xenotransplant Model

PAEC were plated in 96-well microculture plastic plates and grown to confluence in Endothelial-SFM containing 1% fetal calf serum, 0.5 µg/ml amphotericin β and 50 µg/ml gentamycin. The cells were exposed to 100 µl/well of pooled human AB serum at 25–50% (as a source of xenoreactive antibodies and complement) and different concentrations of the anti-C5 MAb 137-76 for 4 hours at 37° C. The cells were washed with PBS and fixed in 0.5% periodate-lysine-paraformaldehyde buffer for 10 minutes at 20° C. The different activation markers were analyzed by means of a cell-based ELISA (CELISA). To measure E-selectin expression, a MAb to human E-selectin (clone 1.2B6, Endogen, Woburn, Mass.) was used. The antibody cross-reacted with the porcine E-selectin (Tsang Y T et al. Porcine E-selectin: cloning and functional characterization. *Immunology* 85: 140–5 (1995)). The cells were incubated with 50 µl of the anti-E-selectin MAb for 45 minutes under constant shaking at 20° C., followed by three washes with PBS. The secondary rabbit anti-mouse Ig (Dako, Glostrup, Denmark) and the final HRP-conjugated swine anti-rabbit Ig (Dako) were applied sequentially after washing in the same manner. The peroxidase substrate solution (1 µg/ml o-phenylenedamine in citrate buffer, pH 5.0, containing 0.015% $H_2O_2$) was added (100 µl/well) and developed in the dark at 37° C. for 10–30 minutes. The color reaction was stopped with 100 µl of 1 M HCl, and the OD was read with a 1420 Multilabel Counter (Victor™, Wallac, Turku, Finland) at 490 nm. The microtiter plates were subsequently washed in tap water, and incubated with 0.1% crystal violet in PBS for 5 min. After a final thorough wash in tap water, 100 µl of 33% acetic acid was used to solubilize the nuclear stain and the OD was determined at 550 nm, representing the actual cell count per well. The data were represented as the OD ratios in order to normalize the number of cells present in each well. The following negative controls were included in the assays: (i) cells incubated with medium alone and stained with anti-E-selectin and (ii) cells incubated with human serum and stained with an isotype and concentration matched control MAb. Cells stimulated with TNF α was used as positive control.

The results show that the anti-C5 MAb 137-76 is very effective in inhibiting type II endothelial cell activation as manifested by the suppression of E-selectin expression on porcine aortic endothelial cells exposed to human serum (FIG. 4).

What is claimed is:

1. A monoclonal antibody MAb 137-76 produced by the hybridoma having ATCC Deposit designation PTA-2581, or a humanized antibody, a chimeric antibody, or a C5 binding fragment thereof.

2. A hybridoma cell line according to claim 1.

3. The C5 binding fragment of the monoclonal antibody of claim 1, wherein the fragment is a Fab, a F(ab')2, Fv, Fd, or a single chain Fv.

4. A composition comprising the monoclonal antibody of claim 1, or a humanized antibody, a chimeric antibody, or a C5 binding fragment thereof, and a physiologically acceptable diluent, carrier, or excipient.

5. A monoclonal antibody MAb 137-30 produced by the hybridoma having ATCC Deposit designation PTA-2582, or a humanized antibody, a chimeric antibody, or a C5 binding fragment thereof.

6. A hybridoma cell line according to claim 5.

7. The C5 binding fragment of the monoclonal antibody of claim 5, wherein the fragment is a Fab, a F(ab')2, Fv, Fd, or a single chain Fv.

8. A composition comprising the monoclonal antibody of claim 5, or a humanized antibody, a chimeric antibody, or a C5 binding fragment thereof, and a physiologically acceptable diluent, carrier, or excipient.

* * * * *